United States Patent [19]

Takenaka et al.

[11] 3,998,867
[45] Dec. 21, 1976

[54] PROCESS FOR THE SIMULTANEOUS PREPARATION OF METHACRYLONITRILE AND 1,3-BUTADIENE

[75] Inventors: Shigeo Takenaka; Hitoshi Shimizu; Akira Iwamoto; Yasuo Kuroda, all of Takasaki, Japan

[73] Assignee: Nippon Kayaku Co., Ltd., Tokyo, Japan

[22] Filed: Nov. 1, 1974

[21] Appl. No.: 520,165

Related U.S. Application Data

[63] Continuation-in-part of Ser. No. 255,129, May 19, 1972, abandoned.

[30] Foreign Application Priority Data

May 26, 1971 Japan .............................. 46-35500

[52] U.S. Cl. .......................... 260/465.3; 260/680 E
[51] Int. Cl.² ................ C07C 120/14; C07C 11/12
[58] Field of Search .......... 260/465.3, 680 E, 403.3

[56] References Cited

UNITED STATES PATENTS 3,414,631 12/1968 Grasselli et al. .................. 260/680
3,642,930 2/1972 Grasselli et al. ................. 260/465.3

Primary Examiner—Joseph P. Brust
Attorney, Agent, or Firm—Russell & Nields

[57] ABSTRACT

This invention relates to a process for simultaneously preparing methacrylonitrile and 1,3-butadiene from a mixture of butanes and butenes (hereinafter referred to as a mixed butane-butene) consisting of isobutane, n-butane, isobutylene, 1-butene, cis-2-butene and trans-2-butene, in excellent selectivity and single pass yield. More particularly, this invention relates to a process for the simultaneous preparation of methacrylonitrile and 1,3-butadiene which comprises subjecting the mixed butane-butene, at high temperatures and in vapor phase, to ammoxidation and oxidative dehydrogenation with a gas containing ammonia and either air or oxygen, using a catalyst of the general formula:

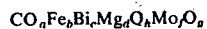

$$Co_aFe_bBi_cMg_dQ_fMo_gO_h$$

wherein Co is cobalt, Fe is iron, Bi is bismuth, Mg is magnesium, Mo is molybdenum, Q is at least one element selected from the group consisting of potassium, rubidium and cesium, O is oxygen, and $a$, $b$, $c$, $d$, $f$, $g$, and $h$ are the number of atoms of Co, Fe, Bi, Mg, Mo, O and Q respectively, with $a$ being a value of from 1 to 15, $b$ from 0.5 to 7, $c$ from 0.1 to 4, $d$ from 0 to 4, $f$ being 12, $g$ being a value of from 39 to 72 determined naturally from the valences of other metal atoms and $h$ from 0.01 to 1.0.

6 Claims, No Drawings

PROCESS FOR THE SIMULTANEOUS PREPARATION OF METHACRYLONITRILE AND 1,3-BUTADIENE

DETAILED DESCRIPTION OF THE INVENTION

This is a continuation-in-part of application Ser. No. 255,129, filed May 19, 1972, now abandoned.

The catalyst of the present invention promotes two synthetic reactions as shown by the following equations:

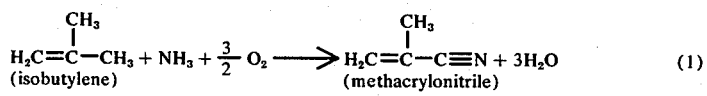

$$\underset{\text{(isobutylene)}}{H_2C=\overset{\overset{\displaystyle CH_3}{|}}{C}-CH_3} + NH_3 + \frac{3}{2}O_2 \longrightarrow \underset{\text{(methacrylonitrile)}}{H_2C=\overset{\overset{\displaystyle CH_3}{|}}{C}-C\equiv N} + 3H_2O \qquad (1)$$

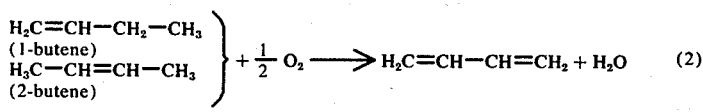

$$\left.\begin{array}{l}\underset{\text{(1-butene)}}{H_2C=CH-CH_2-CH_3}\\ \underset{\text{(2-butene)}}{H_3C-CH=CH-CH_3}\end{array}\right\} + \frac{1}{2}O_2 \longrightarrow H_2C=CH-CH=CH_2 + H_2O \qquad (2)$$

The equation (1) stands for ammoxidation of isobutylene to form methacrylonitrile and the equation (2) for oxidative dehydrogentation of n-butene to form 1,3-butadiene.

Prior to describing the invention in detail, the conversion, selectivity and single pass yield of the present process are defined for the sake of brevity as follows:

$$\text{Conversion } (C) = \frac{\text{Moles of isobutylene (or n-butene) converted}}{\text{Moles of isobutylene (or n-butene) fed}}$$

$$\text{Selectivity } (S) = \frac{\text{Moles of methacrylonitrile (or 1,3-butadiene) produced}}{\text{Moles of isobutylene (or n-butene) converted}}$$

$$\text{Single Pass Yield } (S.P.Y.) = \frac{\text{Moles of methacrylonitrile (or 1,3-butadiene) produced}}{\text{Moles of isobutylene (or n-butene) fed}}$$

BACKGROUND OF THE INVENTION

It is known that isobutylene and n-butene are separately subjected to the vapor phase ammoxidation for synthesizing methacrylonitrile and vapor phase oxidative dehydrogenation for synthesizing 1,3-butadiene, respectively. The former case is described, for example, in Japanese Pat. Nos. 1613/66, 6897/66, 7771/66, 7854/66, 7856/66, 12731/66, 14093/66, 16778/66, 22476/67, 6045/68, 26288/68, 4092/69 and 28491/69, and the latter case is disclosed typically in Japanese Pat. No. 26842/68. However, no report has been known hitherto, as to the simultaneous preparation of methacrylonitrile and 1,3-butadiene by the vapor phase catalytic ammoxidation and oxidative dehydrogenation of mixed butane-butene.

Recently, the production of monomeric ethylene, which is one of the most important petrochemical starting materials, has been carried out in the so-called naphtha cracking center of the petrochemical complex, with the $C_4$ B-B fraction (containing the above-described mixed butane-butene together with butadiene) being formed as a by-product in large amounts. This $C_4$ fraction has heretofore been of little value except for the butadiene and used only as a fuel gas.

With a view to effectively utilizing individual components contained in the $C_4$ fraction, studies have been made individually for synthesis of methacrylonitrile by ammoxidation of isobutylene and for synthesis of 1,3-butadiene by oxidative dehydrogenation of n-butene and, as a result, several patents have been reported.

The processes of these patents require as starting gaseous material isobutylene and n-butene of high purity. Whereas, the constituents of the mixed butane-butene obtained as the B-B fraction, i.e. isobutane, n-butane, isobutylene, 1-butene, wis-2-butene and trans-2-butene are very similar to one another in their physical and chemical properties. Accordingly, separation and purification of these constituents are difficult and make it fairly expensive to produce starting materials of high purity.

Judging from the aspect of starting materials, it is apparent that the present process is advantageous wherein the mixed butane-butene is directly subjected as such to ammoxidation and oxidative dehydrogenation to yield simultaneously methacrylonitrile and 1,3-butadiene.

Thus, the present invention provides a novel and commercially advantageous process which enables the use of fairly low cost starting material, i.e. the $C_4$ fraction formed as by-product on cracking of naphtha, or a residuum obtained after extraction of 1,3-butadiene from said fraction (i.e. the mixed butane-butene).

The two products, methacrylonitrile and 1,3-butadiene, are quite different in chemical properties as the former is a nitrile compound and the latter a diolefin. They are different also in physical properties since methacrylonitrile boils at 90.3° C. and 1,3-butadiene at −4.41° C. This makes it possible to effect separation and purification of these compounds very easily by ordinary distillation, resulting in reduction of cost for the production of useful starting chemicals.

According to the present invention, it has been found that although ammoxidation of isobutylene alone produces methacrylonitrile in a single pass yield of 64.8%, the single pass yield of methacrylonitrile is increased to 75.1% by adding n-butene gas to the reaction system. It has also been found that addition of n-butene results in formation of butadiene and its single pass yield and selectivity are approximately as high as those obtained in oxidative dehydrogenation of n-butene alone.

Although it is not clear why the yield of methacrylonitrile is increased when the ammoxidation and oxidative dehydrogenation are carried out simultaneously using the mixed butene-butane as described above, it is thought that competition between the ammoxidation of isobutylene and oxidative dehydrogenation of n-butene may occur and this competition may decrease the concentration of active sites on the surface of the catalyst for the ammoxidation of isobutylene, and/or strongly active sites on the catalyst may be used for the oxidative dehydrogenation of n-butene, thereby avoiding excessive proceeding of the ammoxidation of isobutylene and resulting in increase in selectivity to methacrylonitrile.

In the catalyst used in the present invention, the numbers of individual atoms is preferably within the following ranges:

$a$: 3–10, $b$: 1–5, $c$: 0.6–2, $d$: 0–3, $h$: 0.04–0.8, $f$: 12 and $g$: 42–68.

The catalyst utilizable in the present invention can be prepared by adding to an aqueous solution of an appropriate molybdate such as ammonium molybdate, at least one of potassium, rubidium, and cesium compounds and then water-soluble iron, bismuth, cobalt, and magnesium compounds, adding, if necessary, a carrier to the resulting slurried suspension, evaporating the mixture to dryness, and treating the resulting cake at high temperatures ranging from 550° to 750° C for 4 hours in the presence of air or oxygen.

Used as the above-described potassium, rubidium, cesium, iron, bismuth, cobalt and magnesium compounds are, for example, nitrates of these metals.

The catalyst may be used as such, i.e. without any carrier to give an excellent yield, although, from the standpoint of catalyst strength, it is preferred to use a small amount of a carrier. Examples of such carriers include inert substances such as silica, silicon carbide and 2-alumina, although the silica is particularly preferred.

The catalyst may be used in the form of granules or tablets.

Although the catalyst may be used in a fixed bed, it is in general desired to use the catalyst in a fluidized or moving bed since the reaction is extremely exothermic.

As molecular oxygen used in the present invention, air is normally employed, although any oxygen-containing gases diluted with an inert gas, e.g. nitrogen which does not affect the desired reaction, may also be used.

Reaction temperatures adopted in the present process may preferably be within the range of from 300° to 500° C and more preferably from 350° to 480° C. The process may be carried out under either superatmospheric or subatmospheric pressure, although it is convenient to conduct the process under normal pressure.

Under real pressure and reaction temperature, contact time of a gaseous mixture consisting of the mixed butane-butene, ammonia and air with the catalyst, is within the range of 0.5–8 seconds, preferably 2–5 seconds.

The mixed gas to be passed through the catalyst is preferably composed of 1–5 moles of oxygen in the form of air and 1–5 moles of ammonia, per mole of effective olefin (i.e. isobutylene plus n-butene) in the mixed butane-butene, and more preferably 1–3 moles of oxygen in the form of air and 1–3 moles of ammonia per mole of the effective olefin. As the desired reaction is exothermal, it is preferred to add 1–30 moles of water in the form of steam.

The present invention will be illustrated in more detail by way of Examples. A carrier ($SiO_2$) is employed in all Examples except Example 19, with the carrier content in the carrier-containing catalyst being between 17 % and 18 % inclusive.

EXAMPLE 1

To a solution of 63.5 g. of ammonium molybdate in distilled water was added 0.230 g. of potassium nitrate with heating and stirring. A suspension of 17.6 g. as $SiO_2$, of Aerosil (Trade name, Nippon Aerosil Co., Ltd.) in water was added to the mixture, and solutions of 61.1 g. of cobalt nitrate and 36.4 g. of ferric nitrate, each dissolved in distilled water, were added. To the resulting suspension was added a solution of 16.4 g. of bismuth nitrate in distilled water acidified with nitric acid and the mixture was stirred under heat and evaporated to dryness on a hot water bath. The residual dry cake was calcined at 700° C for 4 hours in a stream of the air and pulverized to a suitable grain size (about 20 mesh) for use in reaction.

The catalyst thus obtained was represented by a composition $Co_{7.0}Fe_{3.0}Bi_{1.0}K_{0.7}Mo_{12}O_{49}$. Fifty-five ml of the catalyst was filled in a stainless steel reactor of 20 mm i.d. and the reaction was carried out with the reactor immersed in a nitrate bath.

A molar ratio of the effective olefin: $O_2:NH_3:H_2O$ was 1:1.7:1.6:10.8. The effective olefin consisted of 48.5 mol % of isobutylene and 51.5 mol % of 1-butene. The contact time was about 3.8 seconds based on the reaction temperature.

The reaction product was analysed by way of gas-chromatography and found to contain besides methacrylonitrile and 1,3-butadiene as major products, acetonitrile, methacrolein, acetone, acrolein, acetaldehyde, hydrocyanic acid, cis-2-butene (i.e. isomer of 1-butene), trans-2-butene, formic acid, acetic acid, acrylic acid, methacrylic acid and the like formed as by-products.

The results were shown in Table 1.

Table 1

| | | | | |
|---|---|---|---|---|
| Nitrate bath temperature, ° C | 385 | 395 | 417 | 431 |
| Conversion of Mixed butene*,% | 83.1 | 86.8 | 91.9 | 90.5 |
| Selectivity to MN+BD**, % | 71.4 | 76.6 | 78.5 | 82.3 |
| Over-all yield of MN+BD, % | 59.3 | 66.5 | 72.1 | 74.5 |
| Conversion of isobutylene,% | 93.4 | 96.1 | 97.9 | 97.3 |
| Selectivity to methacrylonitrile,% | 59.7 | 68.1 | 69.5 | 77.1 |
| Single Pass Yield of methacrylonitrile, % | 55.8 | 65.5 | 68.0 | 75.1 |
| Conversion of 1-butene,% | 73.4 | 78.2 | 86.2 | 84.1 |
| Selectivity to 1,3-butadiene,% | 84.5 | 86.5 | 88.3 | 88.2 |
| Single Pass yield of 1,3-butadiene,% | 62.0 | 67.6 | 76.1 | 74.2 |

*Conversion of mixed butene = $\dfrac{\text{Moles of isobutylene and 1-butene converted}}{\text{Moles of isobutylene and 1-butene fed}}$

**Selectivity to MN+BD = $\dfrac{\text{Moles of methacrylonitrile and 1,3-butadiene produced}}{\text{Moles of isobutylene and 1-butene converted}}$

Table 1-continued

***Over-all yield of MN+BD = $\dfrac{\text{Moles of methacrylonitrile and 1,3-butadiene produced}}{\text{Moles of isobutylene and 1-butene fed}}$ In the foregoing equations, MN stands for methacrylonitrile and BD for 1,3-butadiene.

COMPARATIVE EXAMPLE 1

Ammoxidation of isobutylene alone was carried out using the catalyst as prepared in Example 1. A molar ratio of the isobutylene: $O_2:NH_3:H_2O$ was 1:3.3:3.6:22. The contact time was 4.0 seconds based on the reaction temperature. Other reaction conditions were the same as in Example 1. The results were shown as follows:
  Conversion of isobutylene = 98.9 %
  Selectivity to methacrylonitrile = 65.5 %
  Single Pass yield of methacrylonitrile = 64.8%

EXAMPLE 2

A catalyst of the composition $Co_7Fe_3Bi_1Mg_1K_{0.07}Mo_{12}O_{50}$ was prepared in the same manner as in Example 1 with the exception that magnesium acetate was further added.

Using the catalyst thus obtained, the reaction was carried out under the same conditions as in Example 1 except for the nitrate bath temperature. The results were shown in Table 2.

Table 2

| | | | |
|---|---|---|---|
| Nitrate bath temperature, ° C | 377 | 390 | 401 |
| Conversion of mixed butene, % | 82.0 | 87.0 | 91.4 |
| Selectivity to MN+BD, % | 77.2 | 75.7 | 74.7 |
| Over-all yield of MN+BD, % | 63.3 | 65.8 | 68.2 |
| Conversion of isobutylene, % | 93.8 | 95.6 | 97.8 |
| Selectivity to methacrylonitrile, % | 70.1 | 66.5 | 65.0 |
| Single pass yield of methacrylonitrile, % | 65.7 | 63.5 | 63.5 |
| Conversion of 1-butene, % | 71.0 | 78.9 | 85.6 |
| Selectivity to 1,3-butadiene, % | 85.9 | 86.3 | 85.1 |
| Single pass yield of 1,3-butadiene, % | 61.0 | 68.0 | 72.9 |

As was apparent from the results shown in Table 2, the optimal reaction temperature for the catalyst in this example was relatively low in comparison with that for the catalyst in Example 1, revealing higher catalytic activity of the former.

EXAMPLE 3

A catalyst of the composition $Co_7Fe_3Bi_1Rb_{0.07}Mo_{12}O_{49}$ was prepared in the same manner as in Example 1 except that rubidium nitrate was used in place of the potassium nitrate. Using the catalyst thus obtained, the reaction was carried out under the same reaction conditions as in Example 1 except for the nitrate bath temperature. The results were shown in Table 3.

EXAMPLE 4

A catalyst of the composition $Co_7Fe_3Bi_1Cs_{0.07}Mo_{12}O_{49}$ was prepared in the same manner as in Example 1 except that cesium nitrate was used in place of the potassium nitrate. Using the catalyst thus prepared, the reaction was carried out under the same reaction conditions as in Example 1 except for the nitrate bath temperature. The results were shown in Table 3.

EXAMPLES 5–13

Using the same starting materials as in Example 1 but varying their amounts used, catalysts of the following various compositions were prepared in a similar manner.

Example

5 $Co_7Fe_3Bi_1K_{0.4}Mo_{12}O_{49}$
6 $Co_7Fe_3Bi_1K_{0.8}Mo_{12}O_{49}$
7 $Co_1Fe_3Bi_1K_{0.07}Mo_{12}O_{43}$
8 $Co_9Fe_1Bi_1K_{0.07}Mo_{12}O_{48}$
9 $Co_1Fe_1Bi_3K_{0.07}Mo_{12}O_{43}$
10 $Co_{14}Fe_1Bi_1K_{0.07}Mo_{12}O_{53}$
11 $Co_1Fe_6Bi_1K_{0.07}Mo_{12}O_{48}$
12 $Co_7Fe_3Bi_1K_{0.03}Mo_{12}O_{49}$
13 $Co_7Fe_3Bi_{0.5}K_{0.07}Mo_{12}O_{49}$

Using these catalysts, the reaction was carried out under the same conditions as in Example 1 except for the nitrate bath temperature. The results were shown in Table 3.

Table 3

| Example No. | 3 | 4 | 5 | 6 | 7 | 8 | 9 | 10 | 11 | 12 | 13 | 14 |
|---|---|---|---|---|---|---|---|---|---|---|---|---|
| Nitrate bath temperature, ° C | 420 | 420 | 450 | 450 | 420 | 430 | 430 | 430 | 420 | 370 | 410 | 390 |
| Conversion of mixed butene, % | 90.3 | 91.6 | 88.5 | 86.4 | 89.1 | 93.0 | 88.6 | 87.3 | 85.6 | 87.2 | 90.2 | 91.1 |
| Selectivity to MN+BD, % | 79.5 | 77.2 | 79.5 | 79.2 | 74.5 | 75.2 | 66.5 | 70.9 | 66.0 | 69.6 | 67.5 | 73.5 |
| Over-all yield of MN+BD, % | 71.1 | 70.8 | 70.3 | 68.4 | 66.4 | 70.0 | 59.0 | 62.0 | 56.5 | 60.6 | 60.9 | 67.0 |
| Conversion of isobutylene, % | 96.5 | 95.1 | 94.5 | 91.3 | 92.3 | 97.1 | 94.7 | 91.3 | 90.1 | 94.6 | 97.5 | 92.1 |
| Selectivity to methacrylonitrile, % | 70.3 | 69.6 | 70.3 | 71.2 | 65.3 | 65.4 | 56.1 | 66.7 | 57.3 | 59.9 | 55.3 | 67.4 |
| Single pass yield of methacrylonitrile, % | 67.8 | 66.2 | 66.4 | 65.0 | 60.3 | 63.5 | 53.1 | 60.8 | 51.7 | 56.7 | 53.9 | 62.1 |
| Conversion of 1-butene, % | 84.5 | 88.3 | 83.1 | 81.9 | 86.1 | 89.3 | 82.4 | 83.4 | 81.9 | 80.3 | 83.5 | 89.9 |
| Selectivity to 1,3-butadiene, % | 89.0 | 84.8 | 88.9 | 87.7 | 84.2 | 85.2 | 78.6 | 75.7 | 74.6 | 80.5 | 80.9 | 80.1 |
| Single pass yield of 1,3-butadiene, % | 75.1 | 74.8 | 73.9 | 71.7 | 72.4 | 76.1 | 64.7 | 63.1 | 61.1 | 64.6 | 67.5 | 72.0 |

EXAMPLE 14

A catalyst of the composition $Co_7Fe_3Bi_1Mg_3K_{0.07}Mo_{12}O_{52}$ was prepared in the same manner as in Example 1 except that magnesium acetate was further added. The reaction was carried out under the same conditions as in Example 1 except for the nitrate bath temperature. The results were shown in Table 3.

EXAMPLES 15-18

Using the same starting materials as in Example 1 but carrying out 4-hour calcination at 550° C, 600° C, 650° C and 750° C, respectively, instead of 700° C, catalysts of the same composition as in Example 1 were prepared. Using each of the catalysts thus prepared, the reactions were carried out under the same conditions as in Example 1 except for the nitrate bath temperature. The results were shown in Table 4.

Table 4

| Example No. | 15 | 16 | 17 | 18 |
| --- | --- | --- | --- | --- |
| Calcination temperature, ° C | 550 | 600 | 650 | 750 |
| Nitrate bath temperature, ° C | 355 | 390 | 420 | 440 |
| Conversion of mixed butene, % | 96.1 | 94.2 | 92.9 | 86.3 |
| Selectivity to MN+BD, % | 63.0 | 73.5 | 79.2 | 73.6 |
| Over-all yield of MN+BD, % | 60.6 | 69.2 | 73.5 | 63.5 |
| Conversion of isobutylene, % | 95.9 | 97.4 | 96.5 | 94.9 |
| Selectivity to methacrylonitrile, % | 47.1 | 59.7 | 70.2 | 60.9 |
| Single Pass yield of methacrylonitrile, % | 45.1 | 58.1 | 67.8 | 57.7 |
| Conversion of 1-butene, % | 96.2 | 91.2 | 89.5 | 84.3 |
| Selectivity to 1,3-butadiene, % | 78.2 | 87.4 | 88.1 | 81.8 |
| Single Pass yield of 1,3-butadiene, % | 75.2 | 79.7 | 78.8 | 69.0 |

EXAMPLE 19

Using the same procedure as in Example 1 but excluding the use of $SiO_2$ as carrier, a catalyst of a general composition $Co_{7.0}Fe_{3.0}Bi_{1.0}K_{0.07}Mo_{12}O_{49}$ was prepared. The reaction was carried out with the catalyst under the same conditions as in Example 1 except for the nitrate bath temperature. The results were shown as follows:

| | |
| --- | --- |
| Nitrate bath temperature, ° C | 470 |
| Conversion of mixed butene, % | 76.1 |
| Selectivity to MN+BD, % | 78.7 |
| Over-all yield of MN+BD, % | 59.9 |
| Conversion of isobutylene, % | 81.3 |
| Selectivity to methacrylonitrile, % | 70.1 |
| Single Pass yield of methacrylonitrile, % | 57.0 |
| Conversion of 1-butene, % | 71.3 |
| Selectivity to 1,3-butadiene, % | 87.9 |
| Single pass yield of 1,3-butadiene, % | 62.7 |

EXAMPLE 20

The reaction was carried out using the same catalyst as in Example 1 and a spent B-B fraction as the mixed butene.

The spent B-B-fraction consisted of 48.5% of isobutylene, 1.6 % of iso-butane, 10.4 % of n-butane, 16.8% of 1-butene, 13.9 % of trans-2-butene and 8.80% of cis-2-butene.

Other reaction conditions were the same as in Example 1 except for the nitrate bath temperature. The results were shown in Table 5.

Table 5

| | | | |
| --- | --- | --- | --- |
| Nitrate bath temperature, ° C | 430 | 450 | 470 |
| Conversion of mixed butene*, % | 81.2 | 84.8 | 87.3 |
| Selectivity to MN+BD**, % | 78.6 | 76.1 | 71.9 |
| Over-all yield of MN+BD***, % | 63.9 | 64.5 | 62.8 |
| Conversion of isobutylene, % | 96.7 | 97.5 | 98.1 |
| Selectivity to methacrylonitrile, % | 73.5 | 70.1 | 64.2 |
| Single pass yield of methacrylonitrile, % | 71.1 | 68.3 | 63.0 |
| Conversion of n-butene, % | 62.1 | 69.1 | 74.3 |
| Selectivity to 1,3-butadiene, % | 88.5 | 86.5 | 83.9 |
| Single pass yield of 1,3-butadiene, % | 54.9 | 59.7 | 62.3 |

Remarks:

*Conversion of mixed butene = $\dfrac{\text{Moles of effective olefin converted}}{\text{Moles of effective olefin fed}}$

**Selectivity to MN+BD = $\dfrac{\text{Moles of methacrylonitrile and 1,3-butadiene produced}}{\text{Moles of effective olefin converted}}$

***Over-all yield of MN+BD = $\dfrac{\text{Moles of methacrylonitrile and 1,3-Butadiene produced}}{\text{Moles of effective olefin fed}}$ In the equations above, the term "effective olefin" was defined as isobutylene, 1-butene, trans-2-butene, and cis-2-butene.

EXAMPLES 21-24

The reactions were carried out using the same catalyst as in Example 1 and the spent B-B fraction having the following composition as the mixed butane-butene:

| | | Example 21 | Example 22 | Example 23 | Example 24 |
| --- | --- | --- | --- | --- | --- |
| Spent B—B fraction | | | | | |
| isobutylene | (%) | 41.9 | 35.3 | 80.0 | 10.0 |
| isobutane | (%) | 3.2 | 4.8 | 0.6 | 2.8 |
| n-butane | (%) | 20.8 | 31.2 | 4.0 | 18.2 |
| 1-butene | (%) | 14.5 | 12.2 | 6.6 | 29.3 |
| trans-2-butene | (%) | 12.0 | 10.1 | 5.4 | 24.3 |
| cis-2-butene | (%) | 7.6 | 6.4 | 3.4 | 15.4 |

Other reaction conditions were the same as in Example 1 except for the nitrate bath temperature. The results are shown in Table 6.

Table 6

| Example No. | | 21 | 22 | 23 | 24 |
|---|---|---|---|---|---|
| Nitrate bath temperature | (° C) | 450 | 450 | 430 | 470 |
| Conversion of mixed butene | (%) | 84.1 | 82.4 | 92.6 | 72.3 |
| Selectivity to MN+BD | (%) | 77.7 | 78.2 | 70.2 | 86.2 |
| Over-all yield of MN+BD | (%) | 65.3 | 64.4 | 65.0 | 62.3 |
| Conversion of isobutylene | (%) | 97.0 | 96.5 | 97.2 | 95.1 |
| Selectivity to methacrylonitrile | (%) | 72.1 | 71.3 | 68.1 | 71.1 |
| Single pass yield of methacrylonitrile | (%) | 70.0 | 68.8 | 66.2 | 67.7 |
| Conversion of n-butene | (%) | 68.4 | 65.0 | 67.4 | 69.0 |
| Selectivity to 1,3-butadiene | (%) | 87.1 | 87.3 | 86.7 | 89.1 |
| Single pass yield of 1,3-butadiene | (%) | 59.6 | 56.8 | 58.4 | 61.5 |

What is claimed is:

1. A process for the simultaneous preparation of methacrylonitrile and 1,3-butadiene from a mixed butane-butene gas containing isobutylene and n-butene, which is a residuum obtained after extraction of 1,3-butadiene from C4 B-B fraction formed as by-product on cracking of naphtha which comprises subjecting such a mixed gas wherein the ratio of butanes and butenes is 4.6–36 : 95.4–64 and the ratio of isobutylene and n-butene is 12.7–83.9 : 87.3–16.1 at a high temperature and in vapor phase to catalytic ammoxidation and oxidative dehydrogenation using oxygen and ammonia in the presence of a catalyst

$Co_a Fe_b Bi_c Mg_d Q_h Mo_f O_g$ wherein Co, Fe, Bi, Mg, Mo and O are chemical symbols representing cobalt, iron, bismuth, magnesium, molybdenum and oxygen, respectively, Q is at least one element selected from the group consisting of potassium, rubidium and cesium and $a, b, c, d, f, g,$ and $h$ are the number of atoms of Co, Fe, Bi, Mg, Mo, O and Q, respectively, with $a$ being a value of from 1 to 15, $b$ from 0.5 to 7, $c$ from 0.1 to 4, $d$ from 0 to 4, $f$ being fixed at 12, $g$ being a value of from 39 to 72 determined naturally from the valences of other metal atoms, and $h$ from 0.01 to 1.0, the reaction being carried out at a temperature of from 300° C to 500° C, whereby there is produced methacrylonitrile and 1,3-butadiene in a ratio of 13.8–85.5 : 86.2–14.5 said catalyst being prepared by adding to aqueous solution of ammonium molybdate, at least one of potassium compound, rubidium compound and cesium compound and bismuth nitrate and water-soluble compounds of iron, cobalt and, optionally magnesium, evaporating the mixture to dryness, and treating the resulting cake at high temperatures ranging from 550° to 750° C in the presence of air or oxygen.

2. The process of claim 1, wherein
 a is 3–10
 b is 1–5
 c is 0.6–2
 d is 0–3
 f is 12
 g is 42–68
 h is 0.04–0.8

3. The process of claim 1, wherein the catalyst is incorporated on a silica carrier.

4. The process of claim 1, wherein the catalyst is calcined at a temperature of from 550° C to 750° C.

5. The process of claim 1, wherein the reaction is carried out in the presence of steam.

6. The process of claim 1, wherein the molar ratio of oxygen, ammonia, steam and total olefins is 1–5 : 1–5 : 1–30 : 1.

* * * * *